United States Patent [19]

Murata et al.

[11] Patent Number: 5,348,875
[45] Date of Patent: Sep. 20, 1994

[54] **PRODUCTION OF ALGINASE FROM *ENTEROBACTER CLOACAE* M-1 (FERM BP-2577)**

[75] Inventors: Katsumi Murata, Tokyo; Kazuo Murakami, Ibaraki; Isao Kusakabe, Chiba; Toshihide Satoh, Ibaraki, all of Japan

[73] Assignees: Kabushikikaisha Kibun Shokuhin; Kabushikikaisha Kibun Foodchemifa, both of Tokyo, Japan

[21] Appl. No.: 132,223

[22] Filed: Oct. 6, 1993

Related U.S. Application Data

[62] Division of Ser. No. 860,601, Mar. 30, 1992, abandoned, which is a division of Ser. No. 445,296, Dec. 4, 1989, abandoned.

[30] Foreign Application Priority Data

Sep. 7, 1989 [JP] Japan .................................. 1-230511

[51] Int. Cl.$^5$ ......................... C12N 9/24; C12N 1/12; C12N 1/00
[52] U.S. Cl. ................................ 435/200; 435/252.1; 435/822
[58] Field of Search ...................... 435/200, 252.1, 822

[56] References Cited

U.S. PATENT DOCUMENTS 4,278,686  7/1981  Corbett et al. ...................... 514/210
4,933,185  6/1990  Wheatley et al. ................... 424/461

OTHER PUBLICATIONS

Isolation of Bacteria Capable of Producing Alginate-Degrading Enzyme from Natural Environment. M. Kitamikado et al, Nippon Suisan Gakkaishi, 55(4), 709–713(1989).

Beunink et al, *Synchronous anaerobic and aerobic*. Appl. Microbiol. Biotechnol., 29: pp. 72–80, 1988.

*Primary Examiner*—David M. Naff
*Assistant Examiner*—Michael V. Meller
*Attorney, Agent, or Firm*—Browdy and Neimark

[57] ABSTRACT

The present invention relates to alginase produced by bacteria belonging to the genus and a process for production thereof and bacteria as well as a method for decomposing alginic acid.

1 Claim, 7 Drawing Sheets

PRODUCTION OF ALGINASE FROM *ENTEROBACTER CLOACAE* M-1 (FERM BP-2577)

This application is a division of co-pending application Ser. No. 07/860,601 filed Mar. 30, 1992 itself a continuation of parent co-pending application Ser. No. 07/445,296 filed Dec. 4, 1989, now abandoned.

BACKGROUND OF THE INVENTION

1. Field of the Invention

The present invention relates to alginase produced by bacteria belonging to the genus Enterobacter and a process for production thereof and bacteria used, as well as a method for decomposing alginic acid.

The alginase of the present invention can be produced in remarkable quantities by *Enterobacter cloacae* M-1 strain. Therefore, alginic acid can be partially decomposed or fully decomposed using this enzyme to modify its physical properties, whereby new products of alginic acid can be prepared or such is helpful for studies on the structure of alginic acid; etc. Thus, the present invention is extremely useful.

2. Prior art and Problem

It is heretofore known that alginase can be produced by bacteria belonging to the genus Flavobacterium, bacteria belonging to the genus Pseudomonas (Japanese Patent Laid-Open No. 59-143597), bacteria belonging to the genus Vibrio (Nippon Suisan Gakkaishi, 55(4), 709–713 (1989)), etc.

However, a demand for alginase is recently increasing in processing, treatment, etc. of alginic acid and an improved method for the production of alginase in a large scale has been desired.

SUMMARY OF THE INVENTION

As a result of extensive investigations with an attempt to survey a bacterial strain capable of producing alginase in a marked quantity, the present inventors have come to isolate one bacterial strain capable of producing alginase in a marked quantity from the soil waste of alginic acid extraction residue.

An object of the present invention is to provide an alginase in an industrial scale. Another object of the present invention is to provide a novel strain capable of producing an alginase.

A further object of the present invention is to provide a method for producing an alginase using the novel strain.

A still further object of the present invention is to provide a method for decomposing alginic acid using the alginase.

That is, the present invention is directed to:

an alginase produced by an alginase-producing bacterium belonging to the genus Enterobacter and capable of splitting off and decomposing alginic acid lyase-wise;

a method for producing an alginase which comprises culturing an alginase-producing bacterium belonging to the genus Enterobacter and collecting the alginase from the culture;

alginase-producing bacterium M-1 strain belonging to the genus Enterobacter; and, a method for decomposing alginic acid which comprises adding to and acting on a solution containing sodium alginate the culture of an alginase-producing bacterium belonging to the genus Enterobacter, treated products thereof, crude enzyme or purified enzyme.

DETAILED DESCRIPTION OF THE PREFERRED EMBODIMENTS

The novel strain isolated from the soil waste of alginic acid extraction residue has been named M-1 strain and taxonomical studies have been made. It has thus been recognized that the strain belongs to *Enterobacter cloacae*. The M-1 strain has been deposited under Accession No. FERM BP-2577 in the Fermentation Research Institute of the Agency of Industrial Science and Technology of Japan.

Bacteriological properties of *Enterobacter cloacae* M-1 strain are as follows.

| Morphology | rod |
|---|---|
| Gram staining | − |
| Spore | − |
| Mobility | + |
| Oxidase | − |
| Catalase | + |
| OF | F |
| Production of gas from glucose | + |
| Production of indole | − |
| Methyl red | − |
| V-P | + |
| Utilization of citrate | + |
| Production of hydrogen sulfide | − |
| Decomposition of urea | − |
| Deamination of phenylalanine | − |
| Decarboxylation of lysine | − |
| Arginine dihydrolase | + |
| Decarboxylation of ornithine | + |
| Liquefaction of gelatin | − |
| Reduction of nitric acid | + |
| ONPG | + |
| Production of yellow pigment | − |
| Production of acid: | |
| Adonitol | − |
| Arabinose | + |
| Inositol | − |
| Sucrose | + |
| Dulcitol | − |
| Sorbitol | + |
| Mannitol | + |
| Melibiose | + |
| Lactose | + |
| Ramnose | + |

*Enterobacter cloacae* M-1 strain proliferates extremely rapidly. With the proliferation of the strain, the activity of alginase increases and reaches the maxim 12 hours after the initiation of the incubation.

As a culture medium of the present bacteria, there is used a medium containing a suitable quantity of sodium alginate and also containing nitrogen sources and inorganic acid salts. Examples of the nitrogen sources are peptone, yeast extract, ammonium sulfate, ammonium nitrate, etc. As the inorganic acid salts, potassium monophosphate, potassium diphosphate, magnesium sulfate and the like can be suitably used.

The culture temperature is between 30° and 40° C. Culture is carried out by aerial spinner culture until the quantity of the enzyme produced reaches the maximum in about 12 hours.

The alginase is produced outside the cells. Thus, the resulting culture solution is centrifuged at about 10,000 G and the supernatant is obtained as an enzyme solution.

The enzyme can be purified from the obtained supernatant by means of fractionation with acetone, fractionation with ammonium sulfate, ion exchange chromatography using DEAE-Sephadex A-50, CM-Sephadex C-50, etc., gel filtration using Bio-Gel P-100, adsorption chromatography using Hydroxyapatite; etc.

Fractionation with acetone was performed by slowly adding 1 of crude enzyme solution to 2 of cold acetone. However, alginic acid remained in the crude enzyme solution precipitated at the same time so that a recovery rate was as considerably low as below 10%.

Fractionation with ammonium sulfate was performed using ammonium sulfate to saturation degrees of 20, 40, 60, 80 and 90%. As the result, the best recovery rate was obtained by precipitation fractionation with 90% saturated ammonium sulfate. The recovery rate was approximately 70%. However, also in this case, about 25% of the activity remained in the supernatant after fractionation with ammonium sulfate.

Ion exchange chromatography was carried out by equilibrating the column with 0.02 M potassium monophosphate buffer (pH 7.8) and supplying the crude enzyme solution dialyzed to the buffer. Elution was effected by NaCl gradient with the same buffer. As the result, the enzyme was eluted as the non-adsorbed fraction by DEAE-Sephadex A-50. Its recovery rate was 65% and a magnification of purification was 15 times. In the case of CM-Sephadex C-50, the enzyme was eluted as the adsorbed fraction. Its recovery rate was 25% and a magnification of purification was 35 times. Since the enzyme was requiring for metal ions, 1 mM calcium was added to the buffer, which was subjected to chromatography using CM-Sephadex C-50 in s similar manner. As the result, the recovery rate and magnification of purification increased to 45% and 90 times, respectively. Gel filtration using Bio-Gel P-100 was carried out by equilibrating the column with 0.02 M potassium monophosphate buffer (pH 7.8) and then supplying the crude enzyme solution. As the result, its recovery rate was 42% and a magnification of purification was 34 times.

Adsorption chromatography was carried out by equilibrating the column with 0.02 M potassium monophosphate buffer (pH 7.8) and then supplying the crude enzyme solution dialyzed to the buffer. Elution was effected by 0.2 M potassium monophosphate buffer (pH 7.8). As the result, its recovery rate was 80% and a magnification of purification was 3.3 times.

In the present invention, the culture supernatant of the enzyme solution, concentrates, crude enzyme in the acetone fractionation, etc., purified enzyme by various means for purification, etc. can all be the alginase of the present invention. They can be used depending upon use.

Next, physicochemical properties of the alginase of the present invention determined by using the supernatant of the alginase solution obtained in Example 1 are shown below.

1. Activity

It acts on alginic acid and splits off and decomposes alginic acid lyase-wise.

2. Substrate Specificity

It splits off and decomposes alginic acid lyase-wise and produces unsaturated uronic acid or oligosaccharide having an unsaturated uronic acid residue.

1% sodium alginate (M/G=0.93) solution (pH 7.8) was mixed with the crude enzyme solution, which had been inactivated by heating at 100° C. for 5 minutes, in a ratio of 1:1. The mixture was made a blank. The reaction solution was subjected to sampling of 200 $\mu$l each every definite time. Subsequently, each sample was measured by TBA reaction. That is, 0.25 ml of 0.125 N $H_2SO_4$ solution containing 0.025 N $HIO_4$ was added to 200 $\mu$l of the sample, which was settled for 20 minutes to allow the sample to oxidize with periodic acid. Then, 0.5 N HCl solution containing 2% sodium arsenite was added to the mixture. By allowing to settle for 2 minutes, the reaction was terminated. Then, 2 ml of 0.3% thiobarbituric acid solution was added thereto and the mixture was heated on a hot bath of 100° C. for 10 minutes to perform condensation. The reaction solution colored red was allowed to cool and absorbancy was measured at 548 nm. In case that the absorbancy at 548 nm exceeded 1.0, the enzyme reaction solution was appropriately diluted with water so that absorbancy by the TBA reaction was adjusted to 1.0 or less, which was provided for measurement.

Figure 1:
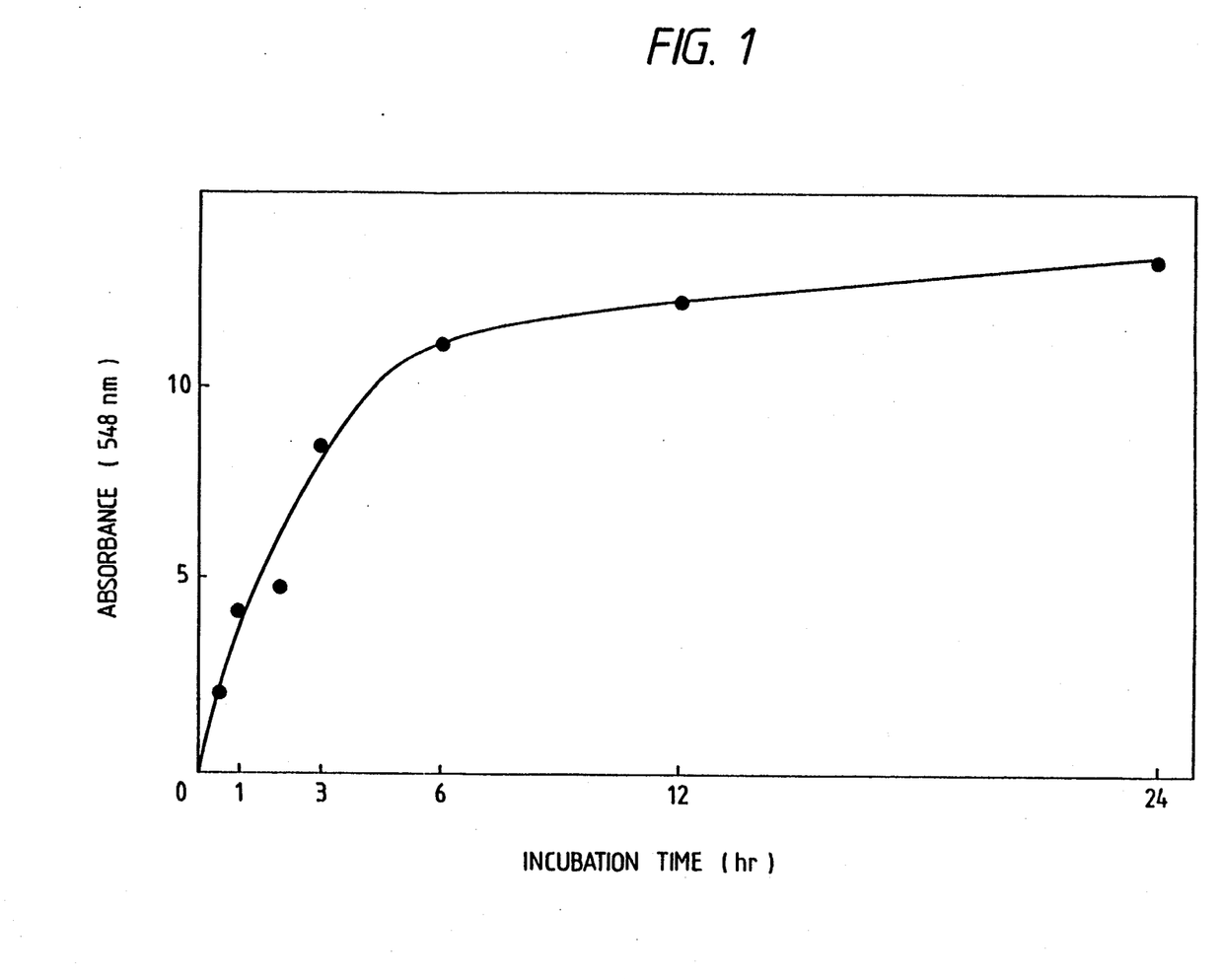
FIG. 1 is a drawing showing the results of measurement of absorption of the red compound produced by thiobarbituric acid reaction with passage of time, after reacting the supernatant of alginase solution with sodium alginate having an M/G ratio of 0.93.
Figure 2A:
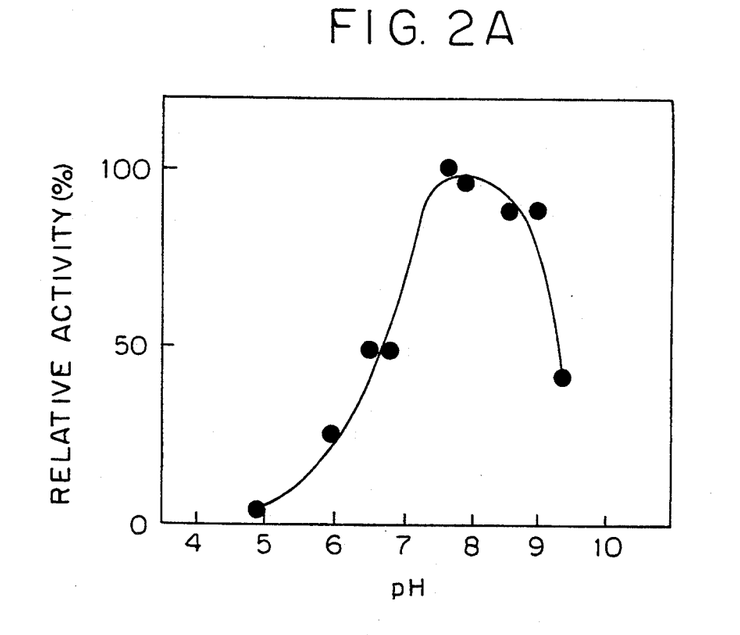
FIG. 2 is a drawing showing acting pH (A), stable pH (B), acting temperature (C) and temperature stability (D), of the enzyme.
Figure 2B:
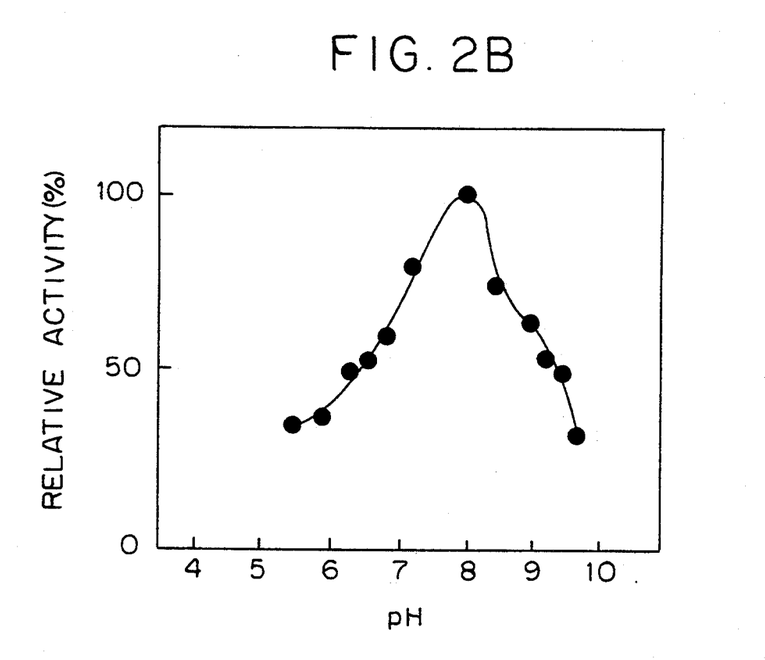
Figure 2C:
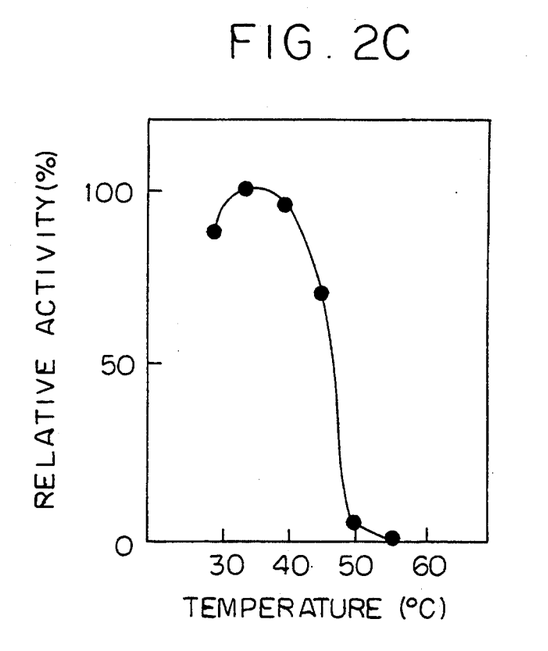
Figure 2D:
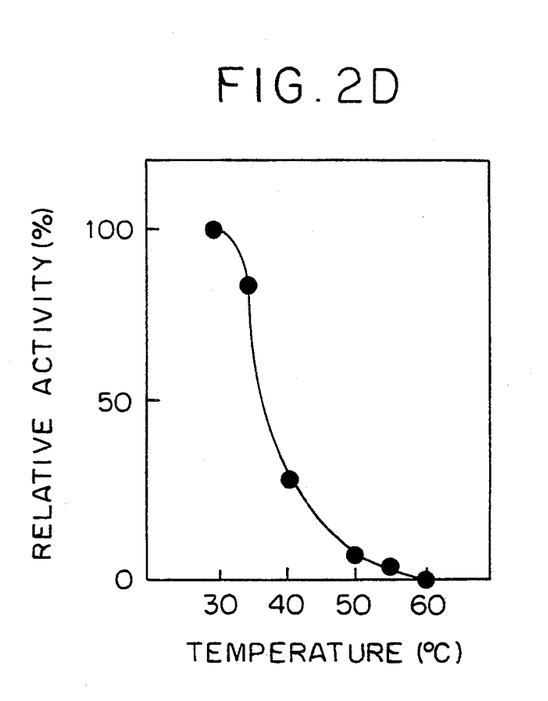

The results are shown in FIG. 1.

As is evident from FIG. 1, the formation of unsaturated uronic acid or oligosaccharide having an unsaturated uronic acid with the present enzyme is almost completed in 6 hours.

Furthermore, the red compound formation system from alginic acid is as shown below.

3. Acting pH and Stable pH

It is shown in FIG. 2 that the optimum pH of the enzyme reaction is 7.8, and stable pH is shown in FIG. 2. In FIG. 2,B, the residual activity of the enzyme after treating at various pH values at 30° C. for 3 hours was stable at pH of about 8 but the stability decreased to less than 50% at pH below 6.5 and pH above 9.

4. Acting Temperature and Temperature Stability

As shown in FIG. 2,C, the optimum temperature of the enzyme reaction is 35° C. The residual activity of the enzyme after treating at various temperatures at pH of 7.8 for 3 hours was stable up to 30° C. but as the temperature increased, the residual activity decreased and was completely lost at 60° C. (FIG. 2,D).

5. Influence of Metal Salts

Figure 3:
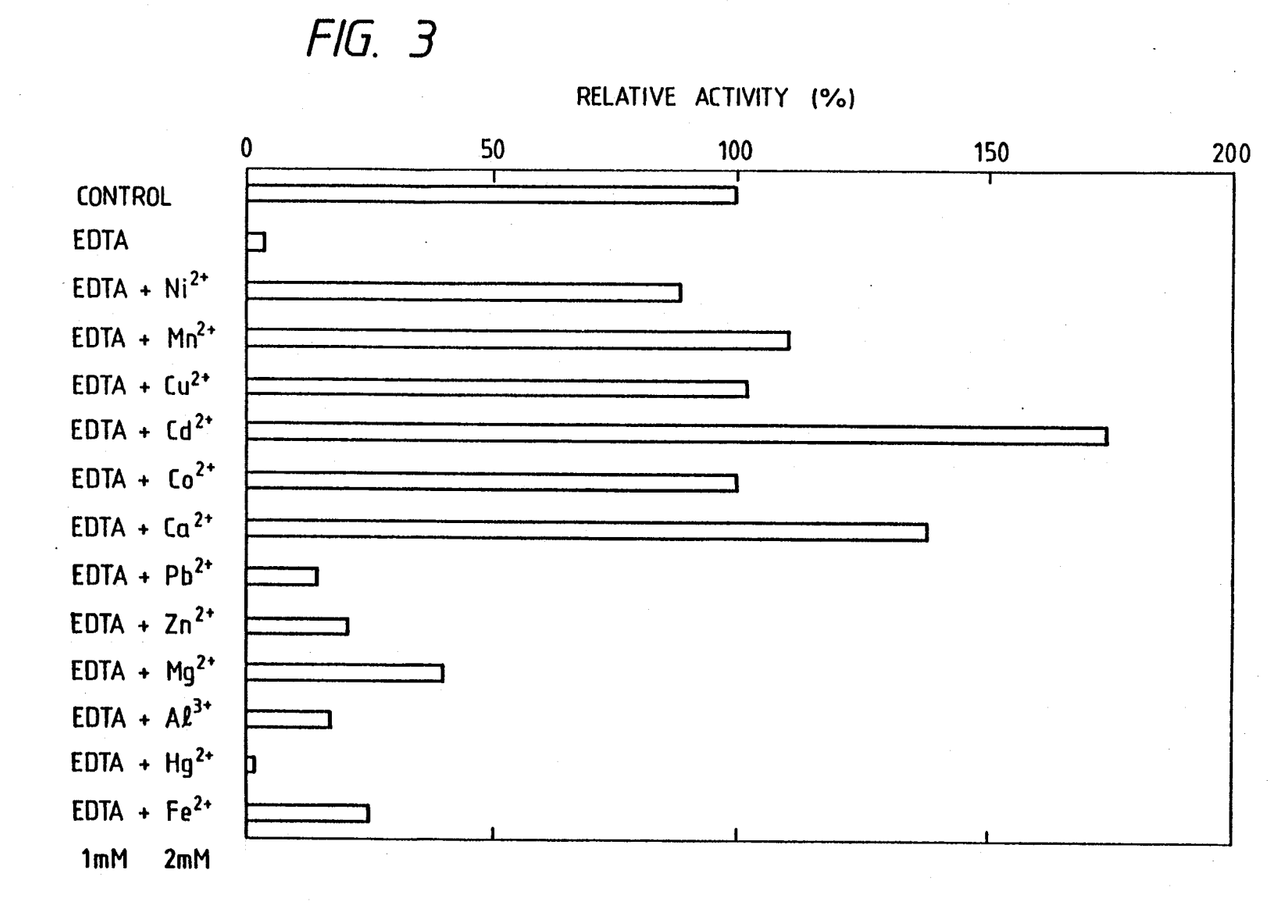
FIG. 3 is a drawing showing inhibition of the enzyme by EDTA and activation by the addition of various metal salts.

Influence of metal salts on the enzyme activity is shown in FIG. 3. The activity of the enzyme was inhibited more strongly by the addition of 1 mM EDTA. However, the activity was markedly activated by the addition of 2 mM cadmium or calcium, etc.

6. Reduction in Viscosity of Sodium Alginate by the Enzyme Action

To 5 ml of 1% sodium alginate solution (pH 7.8) was added 5 ml of the supernatant enzyme solution. Change in viscosity with passage of time was measured at 35° C. with Ostwald viscometer.

Figure 4:
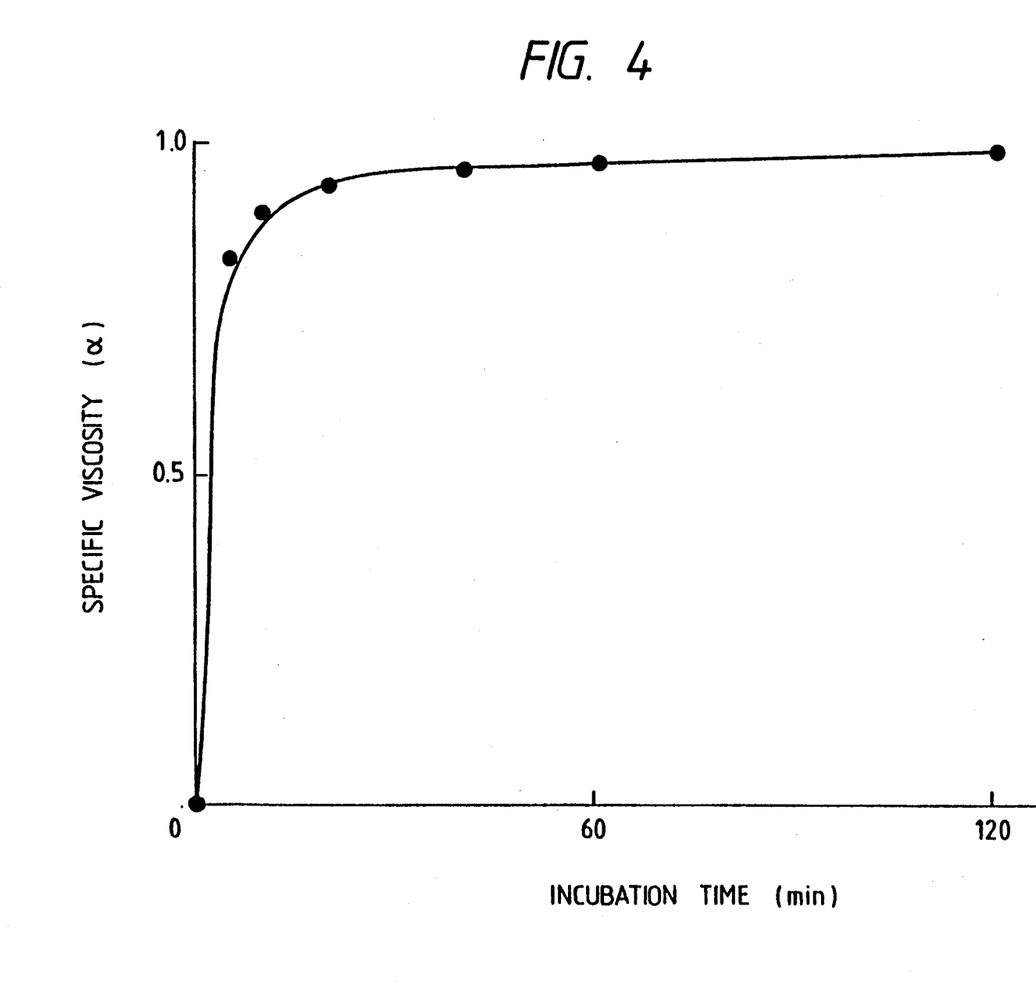
FIG. 4 is a drawing showing reduction in viscosity of sodium alginate by the action of the enzyme.

The results are shown in FIG. 4. Five minutes after, the specific viscosity ($\alpha$) of the reaction solution was 0.83 and 60 minutes after, the specific viscosity reached 0.97. Finally, the viscosity was reduced to almost the same level of pure water.

In FIG. 4:

$$\alpha = \frac{t_0 - t_t}{t_0 - t_w}$$

$t_0$ = time required for the reaction mixture running down at time of 0 (second)

$t_t$ = time required for the reaction mixture running down at time of $t$ (second)

$t_w$ = time for running down of water (second)

7. Decomposition Products of Sodium Alginate

Figure 5:
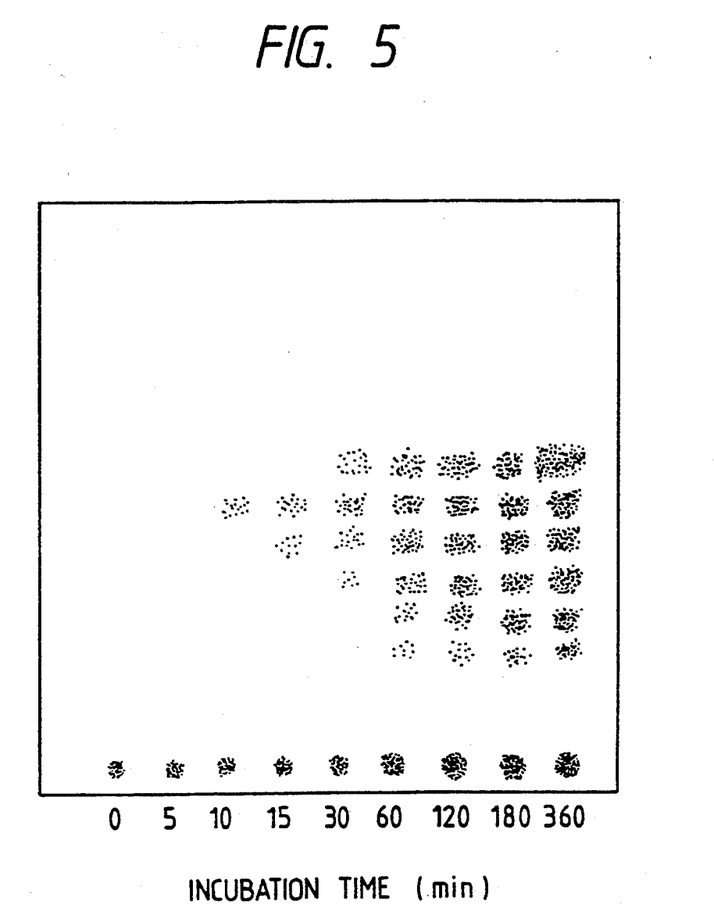
FIG. 5 is a drawing tracing the change of the decomposition products of sodium alginate by this enzyme with passage of time by means of thin layer chromatography.

To 5 ml of 1% sodium alginate solution (pH 7.8) was added 5 ml of the enzyme solution. The mixture was enzymatically reacted at 35° C. The reaction solution was collected with the passage of time and the change of the products was traced by TLC (developing solvent was n-butanol: acetic acid: water=5:2:3). The results are shown in FIG. 5.

8. Thiobarbituric Acid Reaction of the Decomposition Products of Sodium Alginate To 5 ml of 1% sodium alginate solution (pH 7.8) was added 5 ml of the enzyme solution. The mixture was enzymatically reacted at 35° C. The reaction solution was collected with the passage of time and the red compound formed by the thiobarbituric acid reaction was measured at 548 nm. The results are shown in FIG. 1. As the reaction proceeded, the absorbancy at 548 nm rapidly increased. It is thus recognized that the present enzyme is lyase which splits off and decomposes alginic acid.

Next, the present invention is described in more detail by referring to the examples below.

EXAMPLE 1

Composition of medium B: 1.0% sodium alginate, 0.6% peptone, 0.3% yeast extract, 0.5% $KH_2PO_4$ and 0.05% $MgSO_4.7H_2O$.

*Enterobacter cloacae* M-1 strain, FERM BP-2577, was inoculated on medium B having the above composition and shake cultured at 35° C. for 24 hours to give a seed culture solution.

In a culture tank of 10 l was charged 6.4 l of medium B having the above composition. After sterilizing at 120° C. for 20 minutes in an autoclave, the system was cooled to 35° C.

To the medium was inoculated 600 ml of the seed culture solution described above followed by culturing at 35° C. and 350 to 450 rpm in an aerial amount of 1.5 l/min.

Figure 6:
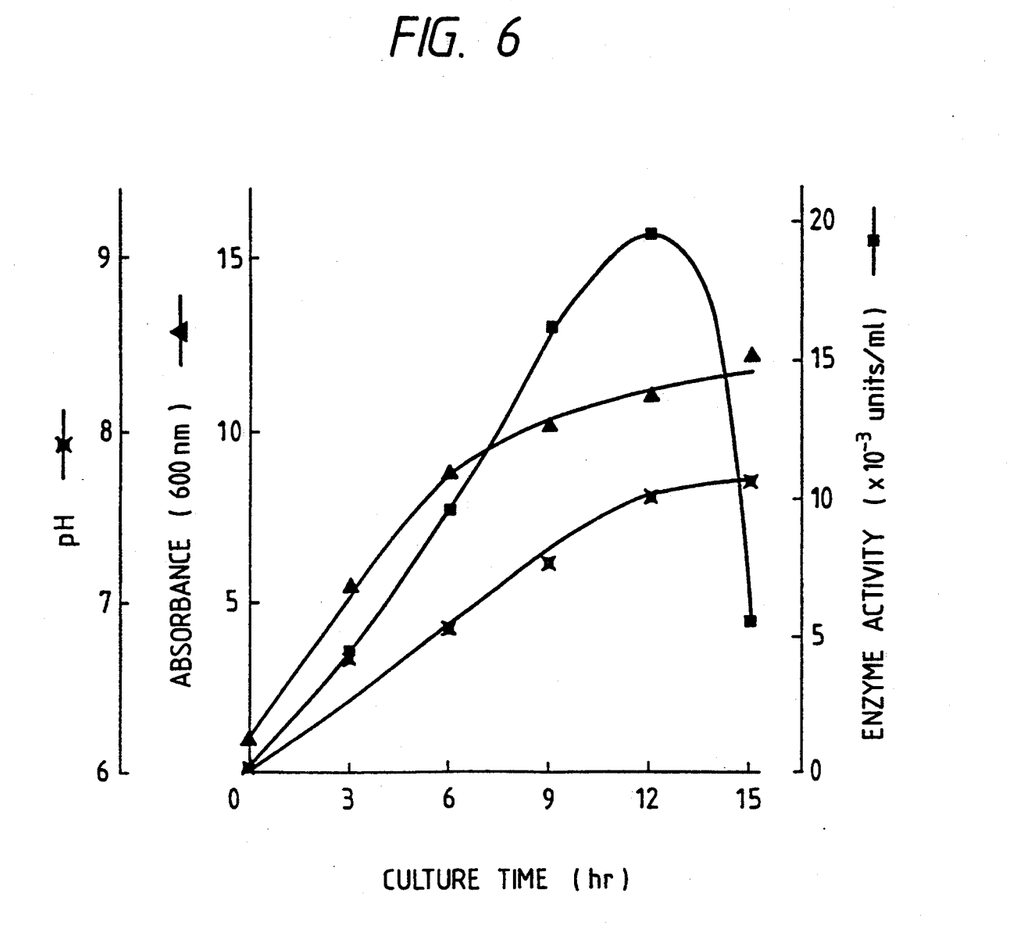
FIG. 6 is a drawing showing the change of culture and enzyme production in Example 1 with passage of time.

The production of the enzyme with passage of time is shown in FIG. 6.

The enzyme production reached the maximum 12 hours after the culture started. After completion of the culture, centrifugation was performed at 10,000 G for 20 minutes to remove the cells. The resulting supernatant was made the alginase solution.

The enzyme activity of the obtained alginase solution was $20 \times 10^{-3}$ u/ml.

The activity of the alginase solution was determined by the following method. In Trishydrochloride buffer containing 1 mM $CaCl_2$ was dissolved sodium alginate in 1% concentration and, 0.5 ml of the enzyme solution was added to 0.5 ml of the resulting solution. The mixture was reacted at 35° C. for 30 minutes and the activity was determined by the thiobarbituric acid method. The enzyme activity was made one unit when the enzyme formed the product corresponding to 1 μmol of uronic acid for one minute under the same conditions.

EXAMPLE 2

To 5 ml of 1% aqueous solution (pH 7.8) of sodium alginate having M/G ratio of D-mannuronic acid (M) and L-gluronic acid (G) of 0.93 was added 5 ml of the supernatant of the alginase solution obtained in Example 1 followed by enzyme reaction at 35° C.

The reaction solution was collected with passage of time and the red compound formed by the thiobarbituric acid method was measured at 548 nm. The results obtained are shown in FIG. 1.

While the invention has been described in detail and with reference to specific embodiments thereof, it is apparent to one skilled in the art that various changes and modifications can be made therein without departing from the spirit and the scope of the present invention.

What is claimed is:

1. A method for producing alginase which comprises culturing *Enterobacter cloacae* M-1, FERM BP-2577 in a medium for twelve hours, obtaining the supernatant by removing the cells by centrifugation and then purifying the supernatant, thereby obtaining alginase.

* * * * *